(12) United States Patent
Gigante

(10) Patent No.: US 11,446,493 B2
(45) Date of Patent: Sep. 20, 2022

(54) DEVICES AND METHODS FOR NERVE STIMULATION

(71) Applicant: Vree Health Italia S.R.L., Rome (IT)

(72) Inventor: Gianluca Gigante, Rome (IT)

(73) Assignee: VREE HEALTH ITALIA S.R.L., Rome (IT)

( * ) Notice: Subject to any disclaimer, the term of this patent is extended or adjusted under 35 U.S.C. 154(b) by 579 days.

(21) Appl. No.: 16/298,479

(22) Filed: Mar. 11, 2019

(65) Prior Publication Data

US 2019/0282813 A1 Sep. 19, 2019

(30) Foreign Application Priority Data

Mar. 16, 2018 (EP) .................................... 18162339

(51) Int. Cl.
| | |
|---|---|
| *A61N 1/36* | (2006.01) |
| *A61B 5/11* | (2006.01) |
| *A61N 1/02* | (2006.01) |
| *A61N 1/04* | (2006.01) |
| *A61N 1/372* | (2006.01) |

(52) U.S. Cl.
CPC ........ *A61N 1/36034* (2017.08); *A61B 5/1106* (2013.01); *A61N 1/025* (2013.01); *A61N 1/0456* (2013.01); *A61N 1/3615* (2013.01); *A61N 1/36031* (2017.08); *A61N 1/36139* (2013.01); *A61N 1/36167* (2013.01); *A61N 1/37247* (2013.01); *A61N 1/37264* (2013.01); *A61B 2562/0219* (2013.01)

(58) Field of Classification Search
CPC .. A61N 1/36034; A61N 1/025; A61N 1/0456; A61B 5/1106; A61B 2562/0219
See application file for complete search history.

(56) References Cited

U.S. PATENT DOCUMENTS

| | | | | |
|---|---|---|---|---|
| 4,817,628 | A * | 4/1989 | Zealear | A61B 5/11 600/595 |
| 5,999,856 | A * | 12/1999 | Kennedy | A61N 1/36039 607/57 |
| 2005/0209644 | A1 * | 9/2005 | Heruth | A61B 5/6826 607/3 |
| 2010/0010391 | A1 * | 1/2010 | Skelton | A61B 5/1116 600/595 |
| 2010/0223020 | A1 * | 9/2010 | Goetz | A61B 5/0031 702/104 |

(Continued)

FOREIGN PATENT DOCUMENTS

| | | |
|---|---|---|
| WO | 2009158495 A1 | 12/2009 |
| WO | 2011156581 A1 | 12/2011 |

OTHER PUBLICATIONS

Organon (Ireland) Ltd., "TOF-Watch SX," Operator Manual, Version 33.512/A, publication date unknown.

*Primary Examiner* — Mallika D Fairchild

(74) *Attorney, Agent, or Firm* — Grady L. White; Potomac Law Group, PLLC

(57) ABSTRACT

A system for nerve stimulation is provided; it comprises a nerve stimulation device configured to execute a set of nerve stimulation instructions for generating electrical pulses for nerve stimulation of a patient. A user electronic device is configured to generate the set of nerve stimulation instructions; and send the set of nerve stimulation instructions wirelessly to the nerve stimulation device.

14 Claims, 7 Drawing Sheets

(56) References Cited

U.S. PATENT DOCUMENTS

| | | | |
|---|---|---|---|
| 2011/0172564 A1* | 7/2011 | Drew | G16H 40/63 |
| | | | 600/587 |
| 2014/0249595 A1 | 9/2014 | Chancellor et al. | |
| 2016/0074662 A1 | 3/2016 | Moffitt et al. | |
| 2016/0361543 A1* | 12/2016 | Kaula | G16H 20/40 |
| 2017/0361093 A1* | 12/2017 | Yoo | A61N 1/36107 |

* cited by examiner

DEVICES AND METHODS FOR NERVE STIMULATION

TECHNICAL FIELD

The present invention relates to devices and methods for nerve stimulation, for example devices for controlling the generation of electrical signals for nerve stimulation of a patient.

BACKGROUND

Nerve stimulation is routine in modern health care. One particular use of nerve stimulation is in the field of anaesthesia. Here the response of a muscle to an electrical stimulation is recorded and the information can be used to monitor the recovery of a patient after receiving an anaesthetic; it is important to monitor any residual paralysis of muscles resulting from the use of neuromuscular blocking drugs which paralyze the patient during the anaesthetic.

Applying an electrical stimulation to a muscle causes the muscle to contract. The force of the contraction is related to the intensity of the electrical stimulation applied. The contracting force of the muscle causes a body part connected to the muscle of the patient to accelerate. An accelerometer connected to the body part can be used to record the resultant acceleration.

Existing devices which able to apply an electrical stimulation to a patient and record a response are known in the field. Examples of existing devices include the TOF-Watch by Organon, the TOF-Cuff NMT monitor by RGB medical devices, and NMT by GE Healthcare. Some of these devices are hand-held and comprise a user interface through which a user, for example a doctor, can control the device to apply an electrical stimulation and measure a response. The electrical stimulation is applied by electrical conductors extending from the device and attached to the patient. However, these devices have a number of shortcomings. For example, a first shortcoming is that the device location in relation to the patient is constrained by the need to be within the length of the electrical conductors from the patient. The conductors need to be relatively short to ensure good conductivity and consistent signalling to the patient—this means that the entire device and the user controlling it needs to be in close proximity to the patient. A second shortcoming is that the devices have to be pre-loaded with pre-configured electrical signal generation programs which cannot be user configured or calibrated, particularly when used in close proximity to the patient.

SUMMARY OF DISCLOSURE

The first aspect of the present invention relates to a system for nerve stimulation. The system for nerve stimulation comprises: a nerve stimulation device configured to execute a set of nerve stimulation instructions for generating electrical pulses for nerve stimulation of a patient; and a user electronic device, configured to: generate the set of nerve stimulation instructions; and send the set of nerve stimulation instructions wirelessly to the nerve stimulation device. Having a separate user electronic device in wireless communication with the nerve stimulation device allows a user to control the nerve stimulation device without being in close proximity to the patient or the nerve stimulation device. Additionally, the nerve stimulation device itself may be kept in close proximity to the patient and so any electrical conductors may be relatively short to ensure good conductivity and consistent signalling to the patient.

In some embodiments, the nerve stimulation device generates one or more electrical pulses for application to a patient corresponding to the set of nerve stimulation instructions. Using a single set of nerve stimulation instructions to generate one or more electrical pulses, in other words a complete program of pulses defined by a single instruction signal, is advantageous since the application of the one or more electrical pulses by the nerve stimulation device to the patient is not affected if the connection between the user electronic device and the nerve stimulation device is interrupted during the program. Additionally, it enables the interval between pulses to be less than the operating frequency of the wireless communication protocol by which the user electronic device and the nerve stimulation device communicate.

The set of nerve stimulation instructions may comprise one or more instructions indicative of: a number of electrical pulses to be generated by the nerve stimulation device; an intensity of the one or more electrical pulses to be generated by the nerve stimulation device; a duration of each of the one or more of the electrical pulses to be generated by the nerve stimulation device; and an interval between the one or more electrical pulses to be generated by the nerve stimulation device. This gives the user great freedom in defining the form of the one or more electrical pulses.

In some embodiments, wherein the user electronic device comprises a memory storing data of one or more preconfigured sets of nerve stimulation instructions. Storing preconfigured sets of nerve stimulation instructions at the user electronic device enables the user to more quickly select and apply a one or more electrical pulses to a patient than defining instructions for one or more electrical pulses from scratch each time. This may be particularly useful when certain sets of nerve stimulation programs are regularly used. Moreover, the preconfigured sets of nerve stimulation instructions could be defined and stored by a user so that they may quickly access preferred sets of nerve stimulation instructions. Additionally parameters of the preconfigured instructions may be adjusted allowing a user to quickly supply a standard set of instructions with minor modifications.

In some embodiments, the nerve stimulation device comprises: a housing; at least two electrical conductors extending from the housing each adapted to be connected to an electrode and for supplying the one or more electrical pulses therebetween via a patient to which the electrodes are attached in use.

The nerve stimulation device may further comprise a connector extending from the housing connected to an acceleration sensor, wherein the acceleration sensor is adapted for attachment to the patient. The nerve stimulation device therefore provides a single central location from which both the electrical conductors and the connector extend. This ensures that the area around the patient is kept clear of unnecessary devices.

The nerve stimulation device may be configured to generate a set of one or more acceleration measurements from one or more accelerations detected by the acceleration sensor.

The nerve stimulation device may be configured to send the set of acceleration measurements to the user electronic device. Generating and sending a complete set of acceleration measurements to the user electronic device from one or more accelerations, is advantageous since the application of the one or more electrical pulses by the nerve stimulation device to the patient is not affected if the connection between the user electronic device and the nerve stimulation device is interrupted during the program.

The user electronic device may be configured to store data of the measured results in a user specific data structure. This allows the user to store measurements for future reference which may allow the user, who may be a doctor, to supply better treatments to the patient in the future. Moreover, the claimed user electronic device may have improved capability to store measurements compared to earlier devices able to apply an electrical stimulation to a patient. In particular, storing measurements the measurements in a user data structure enables measurements relating to particular patient to be quickly recalled and catalogued amongst data from multiple patients.

In some embodiments, the user electrical device may be configured to send to the nerve stimulation device one or more calibration instructions for generating electrical pulses in a calibration routine of a patient. This allows the system to be calibrated to a patient without requiring the user to be in close proximity to the patient.

The calibration instructions may be predefined calibration instructions, the user electronic device may comprise a memory storing the predefined calibration instructions, and the user electronic device may be configured to send the predefined calibration instructions to the nerve stimulation device. Having a predefined set of calibration instructions allows the user to quickly calibrate the system without having to first define a program of electrical pulses in order to determine a calibration.

The user electronic device may be configured to generate the calibration instructions based on the one or more acceleration measurements. This allows the most appropriate calibration instructions to be generated since the actual one or more acceleration measurements are accounted for. This may increase the speed of the calibration procedure, for example.

In some embodiments, wherein the nerve stimulation device is configured to store built-in calibration instructions not sent from the user electronic device. Having built-in calibration instructions allows the user to quickly calibrate the system without having to first define a program of electrical pulses in order to determine a calibration. Moreover, storing the built-in calibration instructions at the nerve stimulation device increases the speed and reliability of a calibration procedure since the calibration instructions do not have to be sent wirelessly to the nerve stimulation device.

The user electronic device may be configured to send to the nerve stimulation device an instruction executable to cause the nerve stimulation device to execute the built-in calibration instructions. Sending a single, basic instruction from the user electronic device to the nerve stimulation device to cause execution of the calibration instructions again improves the reliability and speed of the calibration procedure.

The calibration instructions and/or built-in calibration instructions may trigger the nerve stimulation device to generate a series of electrical pulses of increasing intensity and to record resulting acceleration measurements following generation of each electrical pulse or series of electrical pulses.

The nerve stimulation device may be configured to determine a maximum electrical pulse intensity as the intensity of an electrical pulse at which the resulting acceleration measurements reach a constant value. Having the nerve stimulation device perform the analysis of the acceleration measurements reduces the amount of data that must be communicated back to the user electronic device. This reduces the amount of time required to communicate data and increases the speed of the procedure.

Alternatively, the user electronic device may be configured to determine a maximum electrical pulse intensity as the intensity of an electrical pulse at which the resulting acceleration measurements reach a constant value. Having the user electronic device perform the analysis of the acceleration measurements reduces the amount of processing capacity required by the nerve stimulation device. This may allow the nerve stimulation device to be manufactured at a reduced cost.

A second aspect of the invention pertains to a nerve stimulation device. The nerve stimulation device comprises: a housing; a short range wireless communication transceiver configured to receive nerve stimulation instructions from a user electronic device, and an electrical pulse generator configured to generate one or more electrical pulses corresponding to the received nerve stimulation instructions.

In one embodiment the nerve stimulation device further comprises at least two electrical conductors extending from the housing each adapted to be connected to an electrode and for supplying the one or more electrical pulses therebetween via a patient to which the electrodes are attached in use.

In another embodiment the nerve stimulation device further comprises at least two electrodes for supplying the one or more electrical pulses therebetween via a patient to which the electrodes are attached in use.

A third aspect of the invention pertains to a user electronic device. The user electronic device comprises: processing circuitry configured to generate nerve stimulation instructions; and a short range wireless communication transceiver configured to send the nerve stimulation instructions to a nerve stimulation device based on a wireless communications protocol.

A fourth aspect of the invention pertains to a system for nerve stimulation. The system comprises a nerve stimulation device comprising: a housing; a short range wireless communication transceiver configured to receive nerve stimulation instructions from a user electronic device, and an electrical pulse generator configured to generate one or more electrical pulses corresponding to the received nerve stimulation instructions, and a user electronic comprising: processing circuitry configured to generate nerve stimulation instructions; and a short range wireless communication transceiver configured to send the nerve stimulation instructions to a nerve stimulation device based on a wireless communications protocol.

A fifth aspect of the invention pertains to a method for controlling a nerve stimulation device.

The method for controlling a nerve stimulation device comprises: generating a set of nerve stimulation instructions at a user electronic device; and sending the set of nerve stimulation instructions wirelessly from the user electronic device to a nerve stimulation device for causing the nerve stimulation device to generate electrical pulses for nerve stimulation of a patient.

A sixth aspect of the invention pertains to a computer program. The computer program comprises computer executable instructions which when executed by a processor of a user electronic device cause the user electronic device to perform the steps of generating a set of nerve stimulation instructions at a user electronic device; and sending the set of nerve stimulation instructions wirelessly from the user electronic device to a nerve stimulation device for causing the nerve stimulation device to generate electrical pulses for nerve stimulation of a patient.

BRIEF DESCRIPTION OF THE DRAWINGS

The present invention will now be described with reference to the accompanying drawings, in which.

DETAILED DESCRIPTION

The following detailed disclosure outlines the features of one specific embodiment of the present invention. In addition, some (but by no means all) variants of one embodiment that might be implemented whilst still falling under the scope of the present invention are also described.

Figure 1:
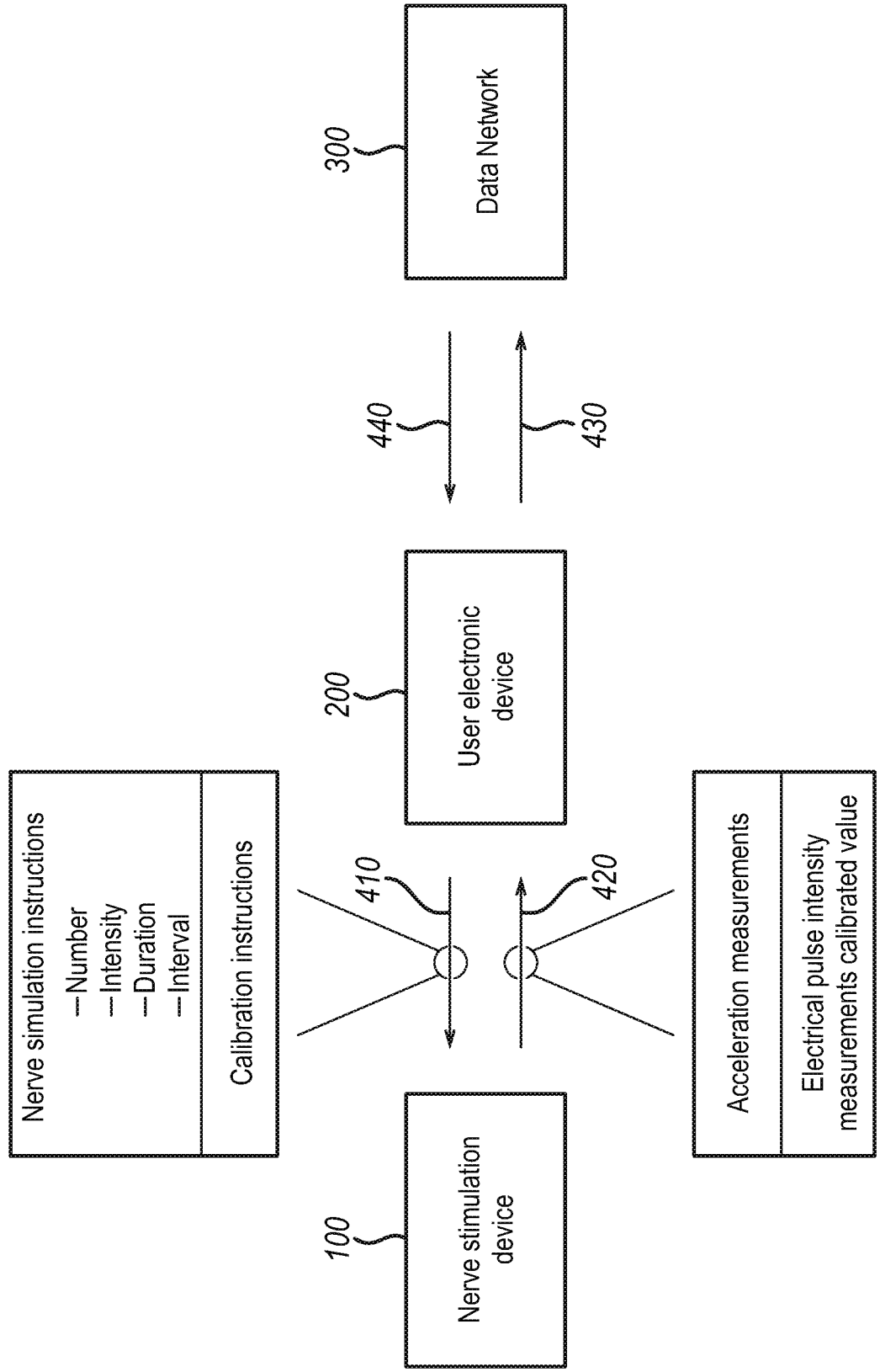
FIG. 1 shows a schematic diagram of a system for controlling a nerve stimulation device.

According to one embodiment of the present invention as shown in FIG. 1, a system for nerve stimulation includes a nerve stimulation device 100 and a user electronic device 200. The nerve stimulation device 100 is configured to execute a set of nerve stimulation instructions. The user electronic device 200 is configured to generate the set of nerve stimulation instructions. The user electronic device 200 is configured to send the set of nerve stimulation instructions wirelessly to the nerve stimulation device. Wireless communication allows the user operating the nerve stimulation device to be spatially separated from the nerve stimulation device. This is advantageous in a crowded operating theatre where physical access to a patient is limited. The nerve stimulation instructions are sent as a nerve stimulation instruction data packet 410. The nerve stimulation device 100 is also configured to send an acceleration measurement data packet 420 back to the user electronic device 200 based on detected accelerations of the patient's body at which an accelerometer is situated. Sending an acceleration measurement data packet back to the user electronic device allows a user to view and analyse the data whilst being spatially separated from the patient and the nerve stimulation device.

The nerve stimulation device 100 generates one or more electrical pulses for application to a patient corresponding to the set of nerve stimulation instructions. The nerve stimulation instructions comprise one of more instructions indicative of a number of electrical pulses to be generated by the nerve stimulation device 100 and instructions indicative of an intensity of the one or more electrical pulses to be generated by the nerve stimulation device 100. The intensity of the one or more electrical pulses can be defined in volts and/or amperes. The nerve stimulation instructions also comprise one of more instructions indicative of a duration of each of the one or more of the electrical pulses to be generated by the nerve stimulation device 100 and instructions indicative of an interval between the one or more electrical pulses to be generated by the nerve stimulation device 100. The nerve stimulation instructions may be instructions for a series of electrical pulses which are sent to the nerve stimulation device as a single nerve stimulation data packet 410. Sending the instructions as a single nerve stimulation data packet means that the series of electrical pulses can continue to be generated by the nerve stimulation device even if the connection between the user electronic device and the nerve stimulation device is interrupted.

The intensity of the one or more electrical pulses may range between 0-1 A, preferably between 0-100 mA, and more preferably between 0-60 mA. The maximum voltage may range between 100-1000 V, and preferably between 200-500 V. More preferably the maximum voltage is 300 V. The Impedance of the system may range between 0-10 KOhm and preferably 0-5 KOhm. At higher impedances the maximum current is reduced. The duration of the one or more electrical pulses may range between 0.001 ms to 30 s, preferably between 0.001 ms and 1 s, preferably between 0.1-0.5 ms, and more preferably between 0.2-0.3 ms. The interval between the electrical pulses may range between 0.001 ms and 100 s, preferably between 0.1 ms and 10 s, and preferably between 1 ms and 1 s. The form of the pulse may be a square-type waveform, a sawtooth-type waveform, a ramp-type waveform or any other type of waveform.

Referring to FIG. 1, the user electronic device 200 can additionally communicate with a data network 300, e.g. the Internet. In particular, the user electronic device 200 sends an outgoing network data packet 430 to the data network 300 (for example, measurement data received by the user electronic device 200). The user electronic device XX200 is further configured to receive an incoming network data packet 440 from the data network 300. Communication with the internet is via WiFi or a mobile connection, for example.

Nerve Stimulation Device

Figure 2:
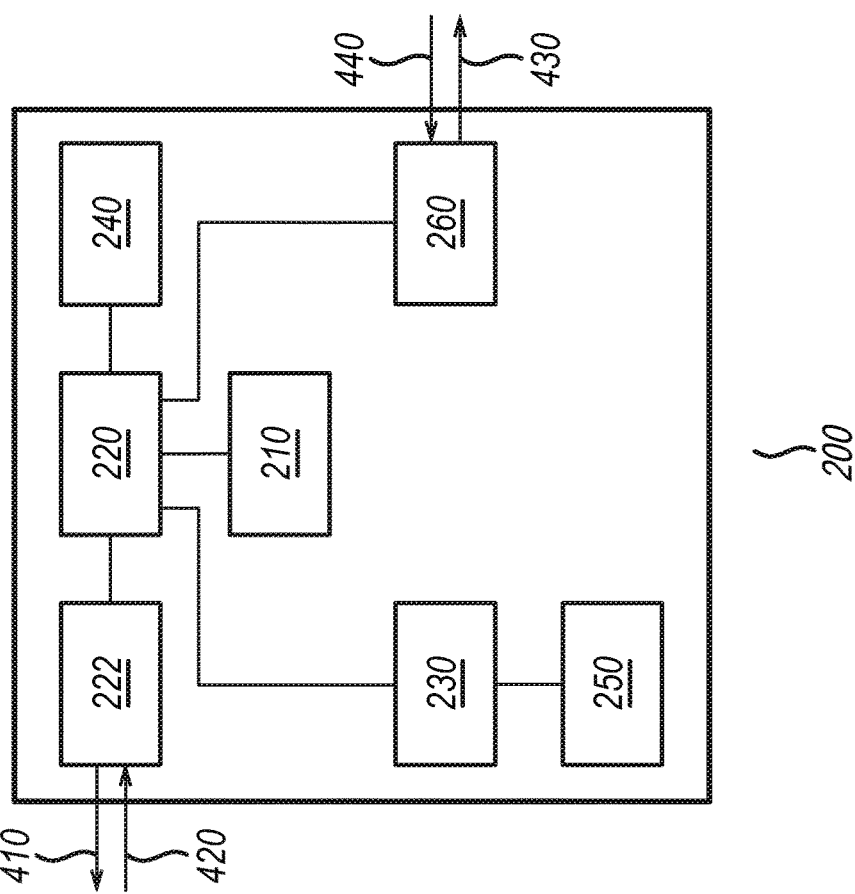
FIG. 2 shows a schematic diagram of the nerve stimulation device of FIG. 1.

FIG. 2 shows a nerve stimulation device in accordance with one embodiment of the present invention. The nerve stimulation device 100 comprises a housing 110 and an electrical pulse generator 160. The electrical pulse generator 160 is located within the housing 110. The electrical pulse generator 160 generates one or more electrical pulses for application to a patient corresponding to the set of nerve stimulation instructions. The electrical pulses are applied to a muscle of the patient which cause the muscle to contract. In one embodiment the electrical pulse generator 160 emits electrical pulses whose intensity is defined in Amps, but, alternatively, it may emit pulses whose intensity is defined in Volts.

The nerve stimulation device 100 comprises a short range wireless communication transceiver 180 which receives the set of nerve stimulation instructions from the user electronic device 200 and sends the acceleration measurements data packet 420 to the user electronic device 200. The short range wireless communication transceiver 180 is located within the housing 110. The short range wireless communication transceiver 180 may implement a Bluetooth™ or equivalent short range wireless protocol.

The nerve stimulation device 100 comprises processing circuitry 190 located within the housing 110. The processing circuitry 190 receives the nerve stimulation instructions from the short range wireless communication transceiver 180. The nerve stimulation device processing circuitry 190 controls the electrical pulse generator 160 based on the received nerve stimulation instructions. This allows the nerve stimulation device 100 to be controlled remotely and avoids the user having to be located close to the nerve stimulation device.

The nerve stimulation device 100 comprises at least two electrodes 130*a,b* for supplying the one or more electrical pulses therebetween to a patient to which the electrodes 130*a,b* are attached in use. The electrodes 130*a,b* have at least one exposed conductive surface for contact with the skin of a patient. The electrodes 130*a,b* are disposed on an outer surface of the housing 110 and the housing is configured for direct contact with a patient's skin.

Alternatively the electrodes 130*a,b* are separate from the housing 110. In this case at least two electrical conductors 120*a,b* extend from the housing 110. The end of each electrical conductor 120*a,b* is adapted to be connected to its respective electrode 130*a,b*. The electrodes 130*a,b* are in the form of patches, clips or grips for attachment to the patient and for holding the at least one exposed conductive surface against the patient's skin. In use, under control of the processing circuitry 190, the electrical pulse generator 160 via the electrical conductors 120*a,b* supplies the electrical pulses therebetween via a patient to which the electrodes 130*a,b* are attached. The electrical conductors 120*a,b* are insulated conductive wires. The electrical conductors 120*a,b* are removably attached to the nerve stimulation device 100. The housing 110 comprises at least two electrical conductor plugs 122*a,b* to which the at least two electrical conductors are removably attached. This allows attachment of different electrical conductors and/or electrodes, if desired by the user who may be a doctor. For example, some electrodes may be more suitable for attachment to particular body parts of the patient than others.

A connector 140 extends from the housing 110 to an acceleration sensor 150. The connector 140 and the acceleration sensor 150 are detachable from the housing 110. The acceleration sensor 150 is adapted for attachment to the patient. In particular the acceleration sensor 150 may be adapted for attachment to the patient's finger or eye and is formed like a clip or a grip to facilitate attachment to the patient. The acceleration sensor 150 is configured to detect acceleration of the body part to which it is attached. The body part will accelerate due to the application of the one or more electrical pulses, which causes a muscle of the body part to contract and move—this movement will be detected by the acceleration sensor 150. The acceleration sensor 150 may be a tri-axial accelerometer. The tri-axial accelerometer allows resolution of the acceleration vector into its components in three-spatial dimensions. Compared to a uni-axial accelerometer this negates the need for calibration and/or grading of the accelerometer itself, increasing the speed of the procedure.

The nerve stimulation device 100 generates a set of acceleration measurements from one or more accelerations detected by the acceleration sensor 150. The nerve stimulation device processing circuitry 190 receives a signal from the acceleration sensor 150 and converts the signal into the set of acceleration measurements. Each measurement within the set corresponds to a particular electrical pulse applied by the generator. The nerve stimulation device 100 sends the set of acceleration measurements to the user electronic device 200 via the short range wireless communication transceiver 180. The short range wireless communication transceiver 180 sends the set of acceleration measurements as an acceleration measurements data packet 420 to the user electronic device. The nerve stimulation device processing circuitry 190 causes the electrical pulse generator 160 to produce the complete series of electrical pulses according to the nerve stimulation instructions, records the resulting complete set of acceleration measurements and sends the complete set of acceleration measurements to the user electronic device 200. In particular, the short range wireless communication transceiver 180 receives a single nerve stimulation data packet 410 comprising nerve stimulation instructions for a complete series of electrical pulses and sends a single acceleration measurements data packet 420 to the user electronic device 200 after the complete series of electrical pulses has been applied. This allows a reliable series of electrical pulses to be generated and acceleration measurements recorded even if the communication between the nerve stimulation device 100 and the user electronic device 200 is interrupted or operates at a lower frequency than the frequency of the electrical pulses.

The nerve stimulation device 100 comprises an electrical pulse intensity measuring means 162 configured to measure the actual intensity of the one or more electrical pulses applied to the patient. A suitable electrical pulse intensity measuring means 162 is an ammeter and/or a voltmeter. The nerve stimulation device processing circuitry 190 receives a signal from the electrical pulse intensity measuring means 162 and converts the signal into a set of electrical pulse intensity measurements. Each measurement within the set corresponds to a particular electrical pulse applied by the generator. The nerve stimulation device 100 sends the set of electrical pulse intensity measurements to the user electronic device 200 via the short range wireless communication transceiver 180. The short range wireless communication transceiver 180 sends the set of electrical pulse intensity measurements in the acceleration measurements data packet 420, optionally together with the set of acceleration measurements. Recording the actual intensity of the electrical pulses allows the user electronic device to perform a more detailed analysis of the electrical pulses applied and their corresponding response. For example, if a lower than anticipated electrical pulse intensity is measured it may explain a reduced acceleration response or indicate a malfunction of the nerve simulation device. The nerve stimulation device is battery powered (battery not shown in figures).

User Electronic Device

Figure 3:
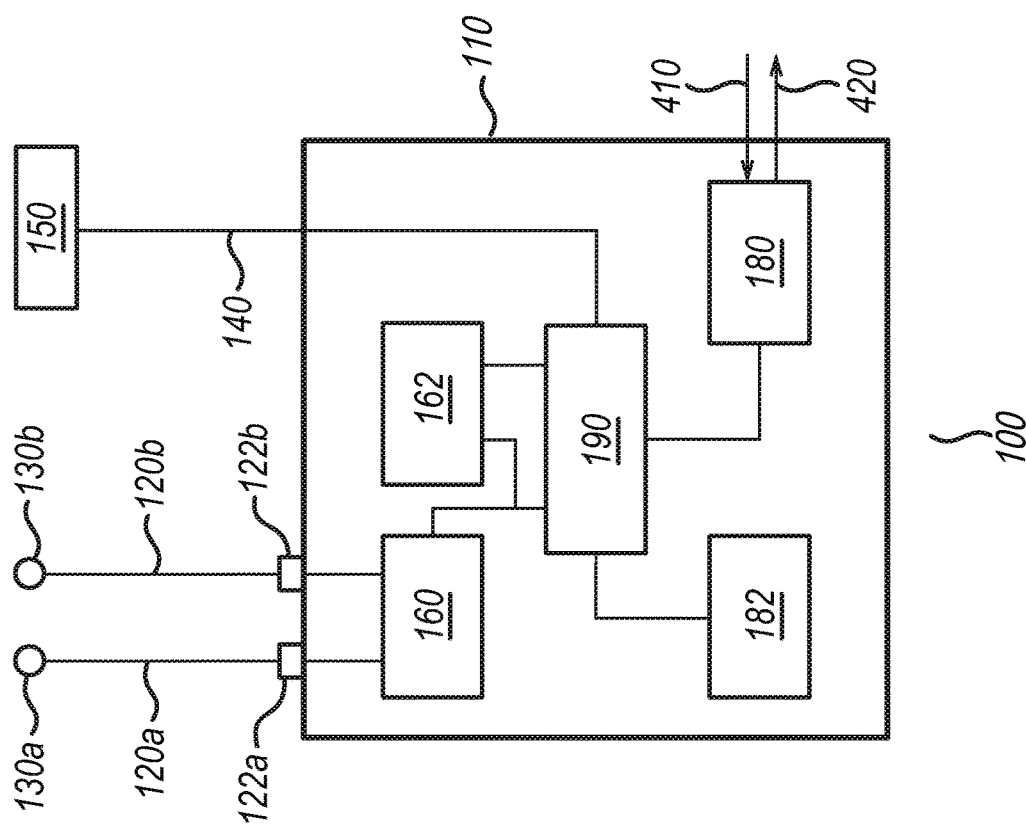
FIG. 3 shows a schematic diagram of the user electronic device of FIG. 1.

FIG. 3 shows a user electronic device 200 in accordance with one embodiment of the present invention. The user electronic device 200 comprises a user electronic device processing circuitry 220 and a short range wireless communication transceiver 222. The user electronic device processing circuitry 220 generates the set of nerve stimulation instructions. The short range wireless communication transceiver 222 is sends the nerve stimulation instructions to the nerve stimulation device 100. The short range wireless communication transceiver 222 sends the set of nerve stimulation instructions to the nerve stimulation device as a nerve stimulation data packet 410. The short range wireless communication transceiver 222 receives a set of acceleration measurements from the nerve stimulation device 100 as an acceleration measurements data packet 420.

The user electronic device 200 comprises a user input interface 210 through which a user interacts with the user electronic device 200 and controls the nerve stimulation device 100. The user input interface 210 is connected to the user electronic device processing circuitry 220. The set of nerve stimulation instructions generated by the user electronic device processing circuitry 220 is generated according to user inputs at the user input interface 210. In particular the user may input one or more user defined sets of nerve stimulation instructions at the user input interface 210. The one or more user defined sets of nerve stimulation instructions are indicative of a number of electrical pulses to be generated by the nerve stimulation device 100, an intensity of the one or more electrical pulses to be generated by the nerve stimulation device 100, a duration of each of the one or more of the electrical pulses to be generated by the nerve stimulation device 100; and an interval between the one or more electrical pulses to be generated by the nerve stimulation device 100. The user electronic device 200 causes at least one set of the one or more user defined sets of nerve stimulation instructions to be selectable from the one or more user defined sets of nerve stimulation instructions for sending as the set of nerve stimulation instructions to the nerve stimulation device. In particular the at least one set of the one or more user defined sets of nerve stimulation instructions is selectable by the user at the user input interface 210.

The user electronic device processing circuitry 220 stores the one or more user defined sets of nerve stimulation instructions in a user specific data structure 250 in response to a user input at the user input interface 210. The user electronic device processing circuitry 220 is configured to load the one or more user defined sets of nerve stimulation instructions from the user specific data structure in response to a user input at the user input interface 210. The user specific data structure is stored in memory of the user electronic device 200 and/or remotely on the data network 300. The user specific data structure 250 is associated with a particular user, e.g. a given patient or doctor. Thus, the user electronic device can store multiple configuration profiles for multiple patients which can be selected via the device. This enables a procedure to be performed more quickly since there is no need to define the procedure from scratch. Additionally, the user specific data structure allows users, such as doctors, to store preferred sets of nerve stimulation instructions specific to them. The user electronic device processing circuitry 220 comprises a search feature to enable data stored in the user specific data to be searched and filtered. This enables a user to quickly find particular stored data.

The user electronic device 200 comprises a memory 230. The memory 230 comprises the user specific data structure 250. The user electronic device processing circuitry 220 is configured to store data from the user specific data structure 250 comprised by the memory 230 of the user electronic device 200 to a second user specific data structure 350 located on the data network 300 in response to a user input at the user interface 210. The user electronic device processing circuitry 220 is configured to load data from the second user specific data structure 350 located on the data network 300 to the user specific data structure 250 comprised by the memory 230 of the user electronic device 200 in response to a user input at the user interface 210. Having at least part of the user specific data structure located at the internet allows more data to be stored since the user specific data structure is no longer confined to the physical specifications of a given user electronic device. Moreover, the user specific data structure located at the internet may be accessed from multiple user electronic devices.

The memory 230 stores data of one or more preconfigured sets of nerve stimulation instructions. The user electronic device 200 is configured to cause at least one set of the one or more preconfigured sets of nerve stimulation instructions to be selectable by a user from the one or more preconfigured sets of nerve stimulation instructions for sending as the nerve stimulation instructions to the nerve stimulation device 100. In particular the at least one set of the one or more preconfigured sets of nerve stimulation instructions is selectable by the user at the user input interface 210.

Figure 4A:
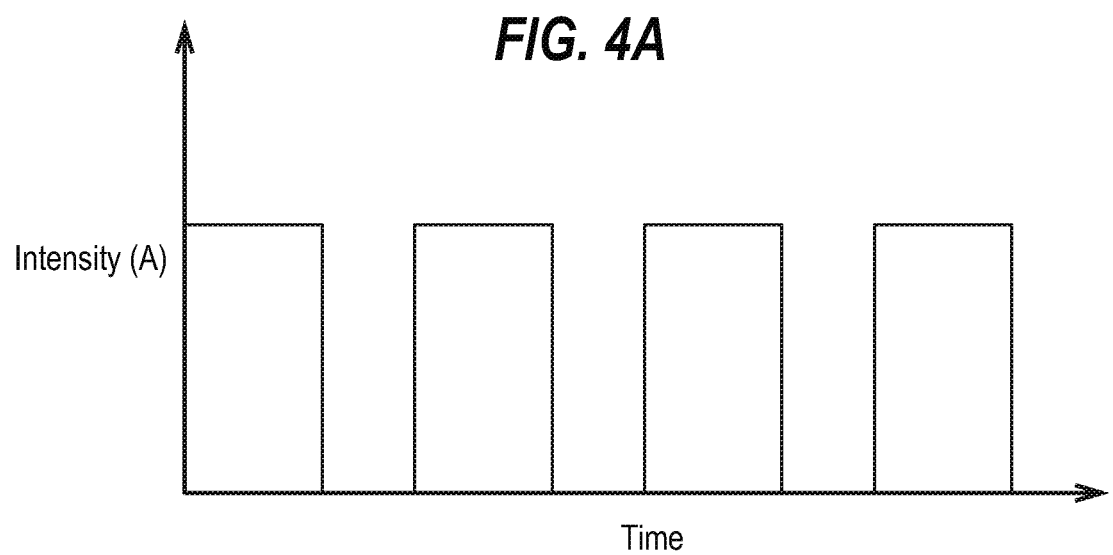
FIGS. 4A, 4B and 4C show exemplary sets of electrical pulses.

The preconfigured sets of nerve stimulation instructions comprises instructions for generating a Train of Four set of electrical pulses at the nerve stimulation device 100. FIG. 4A shows an exemplary Train of Four set of electrical pulses as intensity vs. time. In one embodiment intensity is measured in Amps, but alternatively it may be measured in volts. The Train of Four set of electrical pulses comprises a series of four electrical pulses. Each of the four electrical pulses is of equal intensity and duration. Each of the four electrical pulses has an equal interval between them. Alternatively, the four electrical pulses are of unequal intensity and duration and/or have an unequal interval between them. The user electronic device processing circuitry 220 is configured to allow the intensity of the four electrical pulses to be adjustable, to allow the duration of the four electrical pulses to be adjustable and to allow the interval between the four electrical pulses to be adjustable according to a user input at the user input interface 210.

Figure 4B:
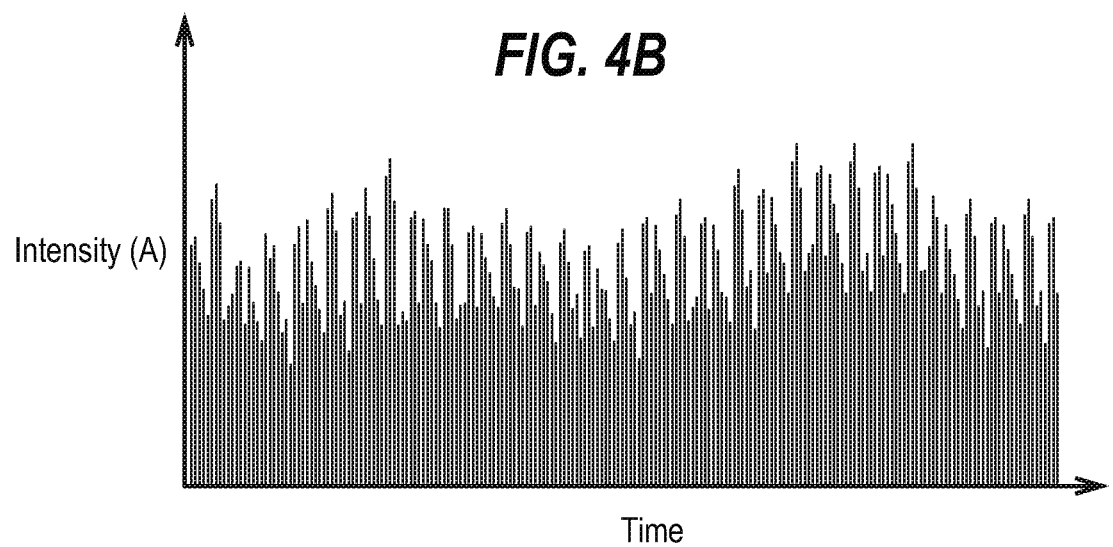

The one of more preconfigured sets of nerve stimulation instructions comprise instructions for generating a Post Tetanic Count set of electrical pulses at the nerve stimulation device 100. FIG. 4B shows an exemplary Post Tetanic Count set of electrical pulses as intensity vs. time. In one embodiment intensity is measured in Amps, but alternatively it may be measured in volts. The Post Tetanic Count set of electrical pulses comprises a series of 250 electrical pulses. Each of the 250 electrical pulses are of equal intensity and duration. Each of the 250 electrical pulses has an equal interval between them. Alternatively, the 250 electrical pulses are of unequal intensity and duration and may have an unequal interval between them. The user electronic device processing circuitry 220 is configured to allow the intensity of the 250 electrical pulses to be adjustable, to allow the duration of the 250 electrical pulses to be adjustable and to allow the interval between the 250 electrical pulses to be adjustable according to a user input at the user input interface 210.

Figure 4C:
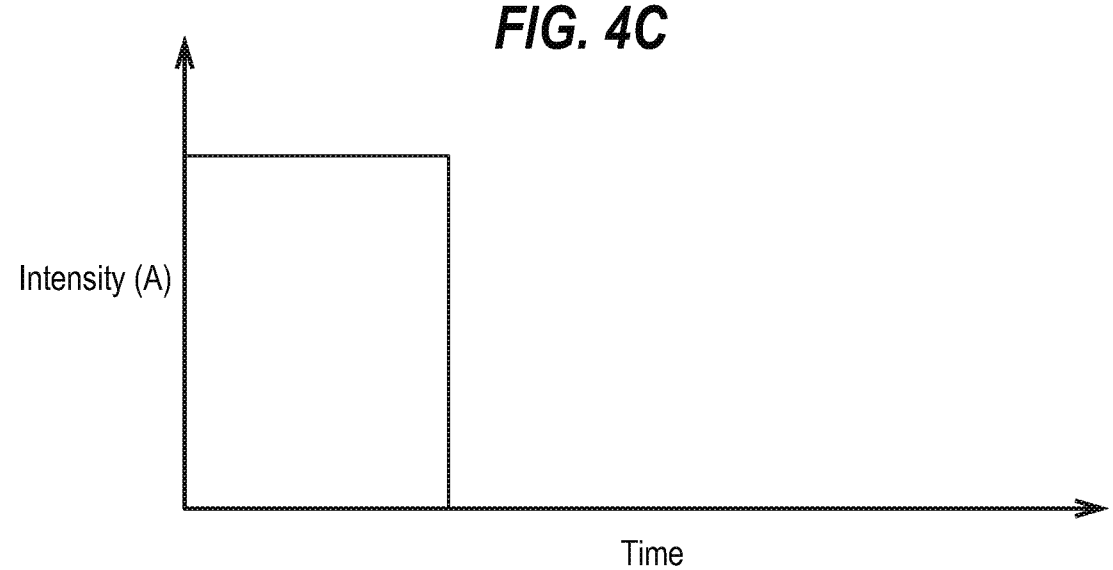

The one of more preconfigured sets of nerve stimulation instructions comprise instructions for generating a Twitch electrical pulse at the nerve stimulation device 100. FIG. 4C shows an exemplary Twitch electrical pulse as intensity vs. time. In one embodiment intensity is measured in Amps, but alternatively it may be measured in volts. The Twitch electrical pulse comprises a single electrical pulse. The user electronic device processing circuitry 220 is configured to allow the intensity of the electrical pulse to be adjustable and to allow the duration of the electrical pulse to be adjustable according to a user input at the user input interface 210.

The memory 230 stores data of instructions for generating a Train of Four set of electrical pulses, data of instructions for generating a Post Tetanic Count set of electrical pulses and/or data of instructions for generating a Twitch pulse as the one or more preconfigured sets of nerve stimulation instructions.

Where multiple electrical pulses are applied, the user electronic device processing circuitry 220 receives the set of electrical pulse intensity measurements from the nerve stimulation device 100. The user electronic device processing circuitry 220 calculates a ratio between the intensity of the first electrical pulse and the last electrical pulse.

The user electronic device 200 comprises a display 240. The display 240 is configured to display the set of acceleration measurements. The display 240 is controlled by the user electronic device processing circuitry 220. The user electronic device processing circuitry 220 is configured to analyse, filter and/or process the set of acceleration measurements before the set of acceleration measurements are displayed. The display displays the one or more of a desired electrical pulse intensity profile corresponding to the set of nerve stimulation instructions, a measured electrical pulse intensity profile corresponding to the set of electrical pulse intensity measurements, and an acceleration measurement profile corresponding to the set of acceleration measurements. The user electronic device processing circuitry 220 causes the ratio between the intensity of the first electrical pulse and the last electrical pulse to also be displayed on the display 240.

The user electronic device processing circuitry 220 is configured to store the set of acceleration measurements and/or the set of electrical pulse intensity measurements in the user specific data structure 250. The user electronic device processing circuitry 220 is configured to load the set of acceleration measurements and/or the set of electrical pulse intensity measurements from the user specific data structure. The user electronic device processing circuitry 220 is configured to store the set of acceleration measurements and/or the set of electrical pulse intensity measurements in the user specific data structure 250 in response to a user input at the user input interface 210. The user electronic device processing circuitry 220 is configured to load the set of acceleration measurements and/or the set of electrical pulse intensity measurements from the user specific data structure in response to a user input at the user input interface 210.

The user electronic device 200 is configured to store user inputted event data pertaining to a patient condition in the user specific data structure 250. The user inputted event data is input at the user input interface 210. User inputted event data comprises an event type, data, time and notes. Examples of event types can be antidote, cardioactive, change temperature and curare, however, these are merely examples and are by no means limiting. In general an event type describes a medical symptom of the patient. The event types may be limited to a preset list, or a user may add more event types. This allows a user to store important medical notes relating to the nerve stimulation in one place together with the nerve stimulation data.

The user electronic device 200 comprises an external communications module 260 for communicating with the data network 300. The external communications module 260 is configured to send an internet outgoing data packet 430 to the data network 300. The external communications module 260 receives an internet incoming data packet 440 from the data network 300. The external communications module 260 communicates with the Internet via WiFi and/or a cellular mobile connection, for example 3G and 4G. The user electronic device 200 may be a phone (mobile or smartphone), tablet device or personal computer.

An advantage of the present invention is that the nerve stimulation device requires a less powerful computer since the nerve stimulation instructions are generated at the user electronic device. This means that the nerve stimulation device processing circuitry 190 can be smaller and lighter weight. Moreover, there is no requirement for a display screen at the nerve stimulation device. This means that the nerve stimulation device of the present invention can be made of smaller size and be lighter in weight than existing devices of the prior art. This means that the devices may be more desirably located about the patient.

Wireless Communication

The nerve stimulation device 100 and the user electronic device 200 communicate via a short range wireless communication protocol. The short range wireless communication protocol may be one of Bluetooth™, infrared, near field communication, ultraband or Zigbee™, however other short range wireless communication protocols are included within the general meaning of this term. Preferably, the short range wireless communication protocol is Bluetooth.

The nerve stimulation device and the user electronic device each comprise a short range wireless communication transceiver. The transceiver 222 of the user electronic device 200 is configured to send the set of nerve stimulation instructions to the transceiver 180 of the nerve stimulation device 100. The transceiver 180 of the nerve stimulation device 100 is configured to send feedback signals, including acceleration measurements and/or the electrical pulse intensity measurements to the transceiver 222 of the user electronic device 200.

The nerve stimulation device 100 is configured to be connected via the short range wireless communication protocol with only one user electronic device 200 at any given time. The nerve stimulation device 100 comprises a user operable input device. When the user operable input device is actuated the nerve stimulation device 100 is placed in a pairing mode for a predetermined pairing time interval. In this time interval, the nerve stimulation device 100 is available for pairing with the user electronic device 200. Pairing involves the exchange of information, for example a passkey to allow the transceiver of the user electronic device 200 to communication with the transceiver of the nerve stimulation device 100. Pairing enables the user electronic device 200 and the nerve stimulation device 100 to communicate. Outside the pairing time interval the nerve stimulation device 100 is not available for pairing with the user electronic device 200. After a given nerve stimulation device 100 has been paired with a given user electronic device 200 they remain paired even if one or both of the devices are switched off or are taken outside the range of the short range wireless communication protocol.

General Use

Figure 8:
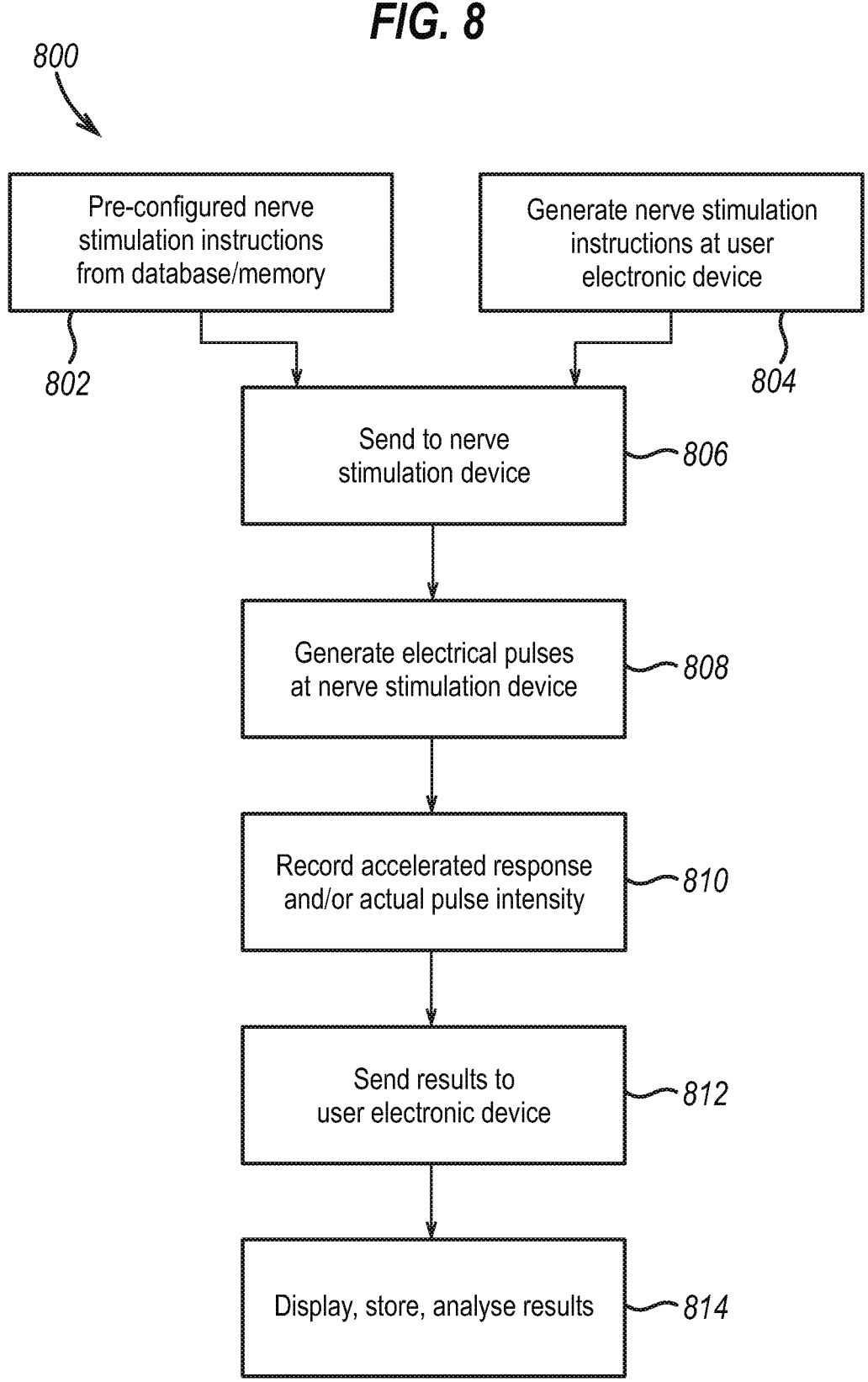
FIG. 8 shows a method of operating the system of FIG. 1.

FIG. 8 shows a method 800 by which the user electronic device 200 is able to control the nerve stimulation device 100. At step 802, the user electronic device 200 may load one or more of the preconfigured sets of nerve stimulation instructions or one of the user defined sets of nerve stimulation instructions from the memory 230. Alternatively, at step 804, the set of nerve stimulation instructions are generated by the user electronic device processing circuitry 220 according to one or more user inputs input via the user input interface 210. At step 806, the one or more nerve stimulation instructions (based on the preconfigured sets, or the one or more user inputs) are sent wirelessly to the nerve stimulation device 100. At step 808, the electrical pulse generator 160, controlled by the nerve stimulation device processing circuitry 190 in response to the received one or more nerve stimulation instructions, generates one or more electrical pulses corresponding to the received one or more nerve stimulation instructions. At step 810, the nerve stimulation device processing circuitry records acceleration measurements (or the electrical pulse intensity measurements received) received back from the acceleration sensor 150 (or electrical pulse intensity measuring means 162). At step 812, the nerve stimulation device sends the set of acceleration measurements and/or the set of electrical pulse intensity measurements to the user electronic device 200 via the wireless communications interface. Finally at step 814, the user electronic device processing circuitry 220 causes the measurements to be displayed on the display 240, stored in the memory 230, analysed, and/or transmitted to a further remote device, e.g. via the Internet, for viewing, processing and/or analysis.

Calibration

The user electronic device 200 is configured to send calibration instructions to the nerve stimulation device 100. This is in response to a user input at the user input interface 210. The user electronic device processing circuitry 220 causes the user electronic device short range wireless communication transceiver 222 to send the calibration instructions to the nerve stimulation device 100.

The memory 230 stores data of predefined calibration instructions. The user electronic device 200 is configured to send the predefined calibration instructions as the nerve stimulation instructions to the nerve stimulation device 100. This is in response to a user input at the user input interface 210. The predefined calibration instructions defines a series of electrical pulses of increasing intensity.

Figure 5:
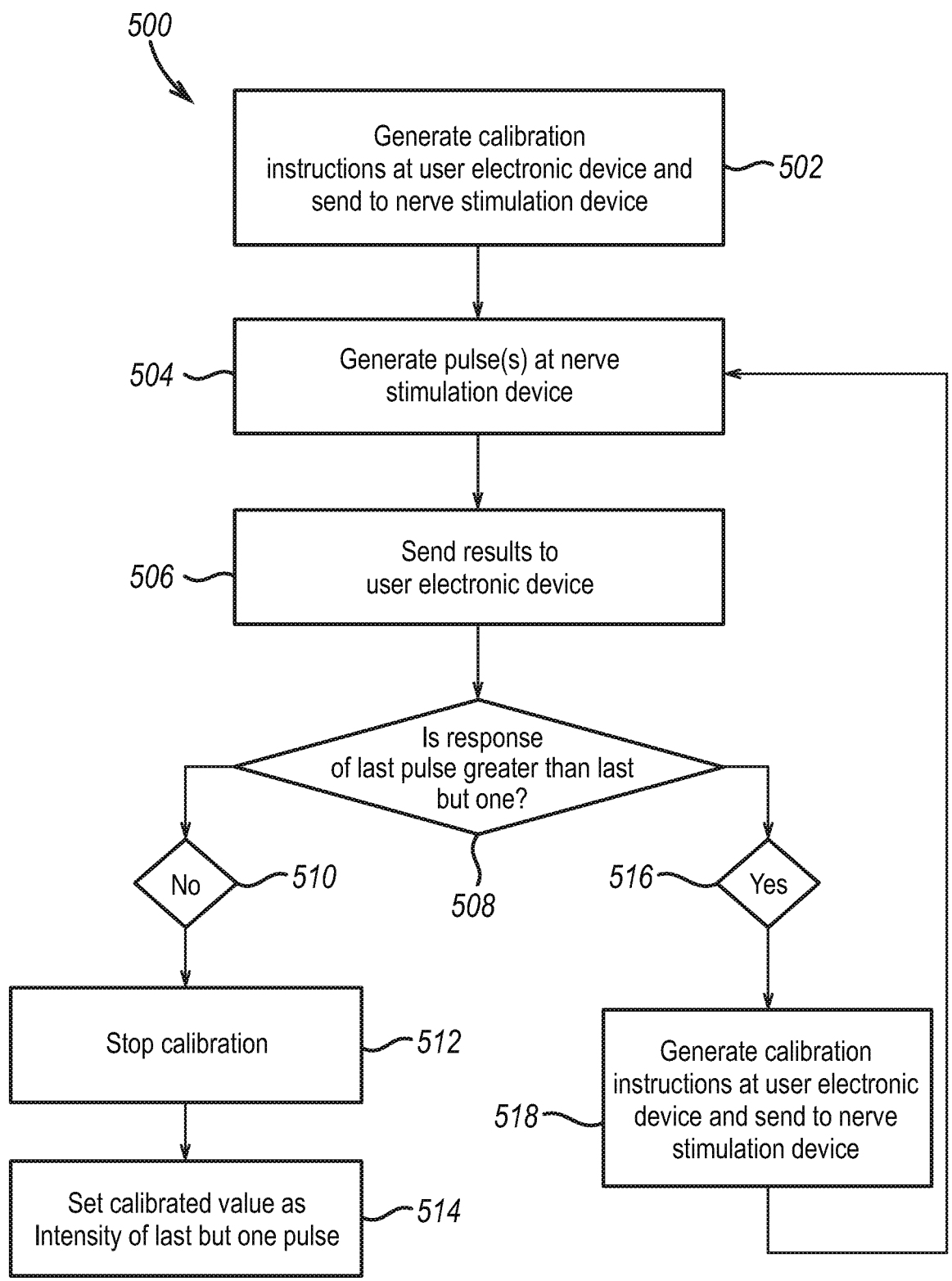
FIG. 5 shows a method of calibrating the system of FIG. 1.

FIG. 5 shows a method 500 of calibrating the nerve stimulation device 100 and the user electronic device 200 in accordance with a specific embodiment of the present invention. At step 502 the user electronic device processing circuitry 220 generates calibration instructions based on the received set of acceleration measurements. The user electronic device 200 sends the calibration instructions to the nerve stimulation device 100 as the set of nerve stimulation instructions. In particular, the user electronic device processing circuity generates a set of calibration instructions defining two electrical pulses of low electrical pulse intensity but where the second electrical pulse is of greater intensity than the first electrical pulse. The calibration instructions are sent to the nerve stimulation device 100 as the set of nerve stimulation instructions and executed at step 504. At step 506 the resulting set of acceleration measurements are sent by the nerve stimulation device 100 and received at the user electronic device 200. At step 508 the user electronic device processing circuitry 220 determines whether the measured acceleration response increases between the two previously applied electrical pulses. At step 518 if the measured acceleration response increases between the two previously applied electrical pulses a new calibration instruction is generated defining a single electrical pulse of greater electrical pulse intensity than the preceding electrical pulse. The calibration instructions are sent to the nerve stimulation device 100 as the set of nerve stimulation instructions and executed at step 506. Again, at step 508, if the measured acceleration response increases between the two previously applied electrical pulses, then steps 504-508 are repeated. If, however, the measured acceleration response is the same between the two previously applied electrical pulses, the process is stopped at step 512 and, at step 514, the electrical pulse intensity of the first of the two previous electrical pulses is taken as the calibrated electrical pulse intensity.

The nerve stimulation device 100 may comprise data of the calibration instructions. The data of the calibration instructions is stored in a nerve stimulation device memory 182. The nerve stimulation device memory is connected to the nerve stimulation device processing circuitry 190.

Figure 6:
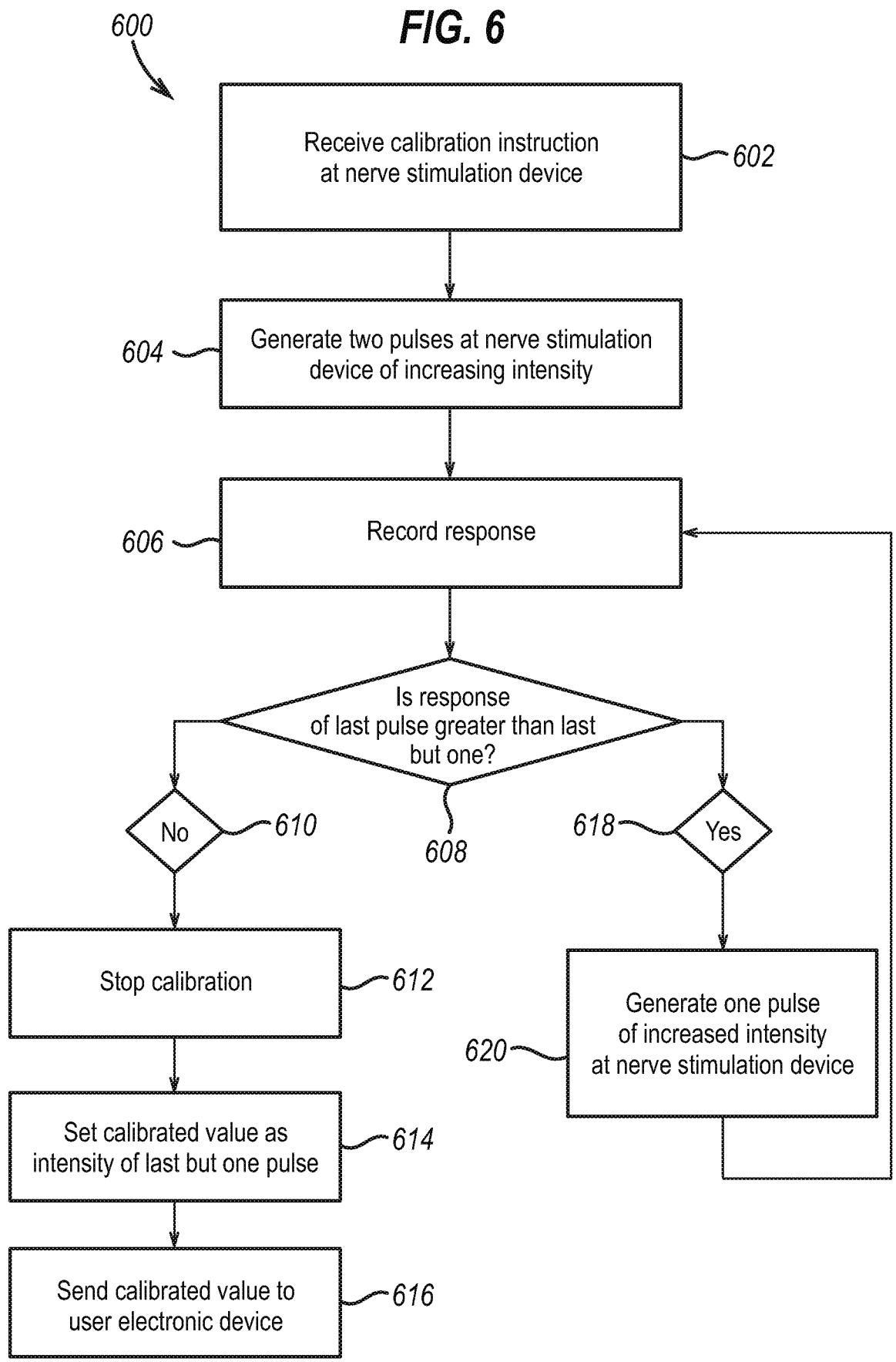
FIG. 6 shows a method of calibrating the system of FIG. 1.

The calibration instructions stored in the nerve stimulation device memory 182 comprises first set of calibration instructions. FIG. 6 shows a method 600 of calibrating the nerve stimulation device 100 and the user electronic device 200 in accordance with one embodiment of the present invention. At step 602 the nerve stimulation device 100 receives an instruction comprised by the nerve stimulation instructions from the user electronic device 200 to cause the nerve stimulation device 100 to execute the first set of calibration instructions stored in the nerve stimulation device memory 182. At step 604 the first set of calibration instructions stored by the nerve stimulation device memory 182 are executed and cause the electrical pulse generator 160 to generate two electrical pulses of low electrical pulse intensity but where the second electrical pulse is of greater intensity than the first electrical pulse. At step 606, the resulting accelerations are recorded as the set of acceleration measurements. At step 608, the nerve stimulation device processing circuitry 190 determines whether the resulting acceleration of the second electrical pulse is greater than that of the first electrical pulse. At step 620, if the measured acceleration response increases between the two electrical pulses, the nerve stimulation device processing circuitry causes the electrical pulse generator 160 to generate an electrical pulse of greater intensity than the preceding electrical pulse. At step 606 the resulting acceleration is recorded. At step 608 the nerve stimulation device processing circuitry 190 determines whether the resulting acceleration of the preceding electrical pulse is greater than that of the last but one electrical pulse At step 608, if the measured acceleration response of the preceding electrical pulse is greater than the intensity of the last but one electrical pulse, steps 620 and 604-608 are repeated. If, however, the measured acceleration response is the same between the two previously applied electrical pulses, at step 612 the process is stopped and, at step 614, the electrical pulse intensity of the first of the two previous electrical pulses is taken as the calibrated electrical pulse intensity. At step 616 the nerve stimulation device processing circuitry 190 sends the calibrated electrical pulse intensity to the user electronic device 200.

Figure 7:
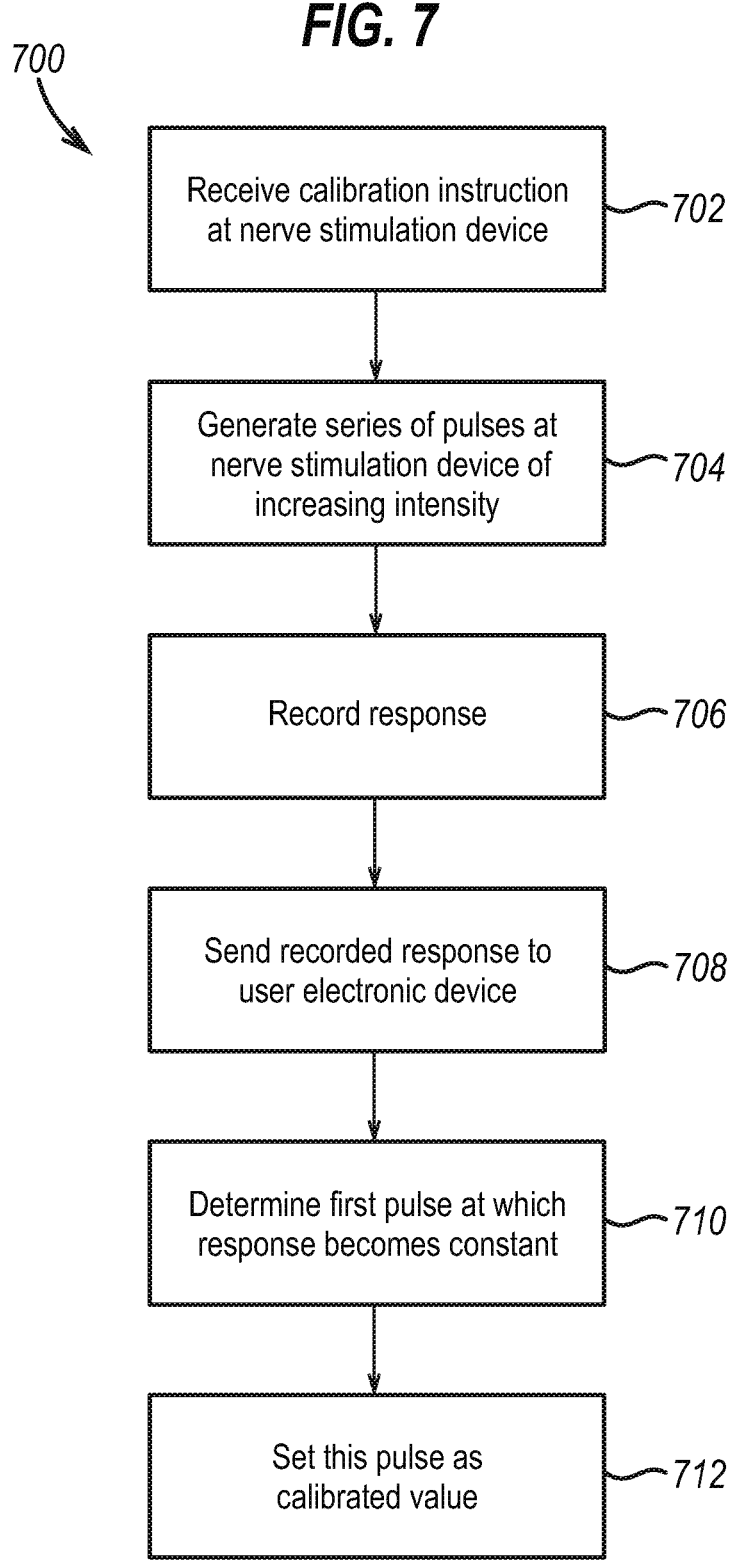
FIG. 7 shows a method of calibrating the system of FIG. 1.

The calibration instructions stored in the nerve stimulation device memory 182 comprises second set of calibration instructions. FIG. 7 shows a method 700 of calibrating the nerve stimulation device 100 and the user electronic device 200 in accordance with one embodiment of the present invention. At step 702 the user electronic device 100 sends an instruction comprised by the nerve stimulation instructions to the nerve stimulation device 100 to cause the nerve stimulation device 100 to execute the second set of calibration instructions stored in the nerve stimulation device memory 182. At step 704 the second set of calibration instructions stored by the nerve stimulation device memory 182 are executed and cause the electrical pulse generator 160 to generate a series electrical pulses of increasing electrical pulse intensity. At step 706, the nerve stimulation device processing circuitry 190 generates a set of acceleration measurements from the accelerations detected by the acceleration sensor 150. At step 708, the nerve stimulation device 100 sends the set of acceleration measurements and the set of electrical pulse intensity measurements to the user electronic device 200 via the short range wireless communication transceiver 180. At step 710, the user electronic device processing circuitry 220 determines the first electrical pulse intensity at which the measured acceleration response stops increasing and becomes constant. At step 712, the first electrical pulse intensity at which the measured acceleration response stops increasing and becomes constant is taken as the calibrated electrical pulse intensity.

The user electronic device processing circuitry 220 is configured to store the calibrated electrical pulse intensity in the user specific data structure 250. The user electronic device processing circuitry 220 is configured to load a calibrated electrical pulse intensity from the user specific data structure 250.

Calibrating the intensity of the one or more electrical pulses to be applied to the patient enables reliable acceleration data to be gathered without subjecting the patient to excessive electrical pulse intensity. If the electrical pulse intensity is too low either no acceleration will be detected or the acceleration measurement will have a poor signal to noise ratio. Increasing the electrical pulse intensity causes a larger acceleration which is more easily detectable and the measurement will have a better signal to noise ratio. However, this is at the expense of subjecting the patient to a larger electrical pulse intensity. In fact, whilst the measured acceleration response initially increases as the electrical pulse intensity increased, eventually the measured response reaches a constant value or plateau even if the electrical pulse intensity is further increased. It has been determined that the electrical pulse intensity at which the measurement acceleration response first begins to plateau is the optimum electrical pulse intensity to be applied to the patient. This calibrated value is found to vary from patient to patient, for example due to different skin resistance, and so the present system and method presents a significant advantage other systems and methods which require the user to manually select or identify the electrical pulse intensity to be applied.

Computer Program

A computer program in accordance with one embodiment of the present invention is configured to be installable on the user electronic device 200 and executed by its processing circuitry. The computer program may be installed in the memory 230 of the user electronic device 200. The computer program is configured to be executed by the user electronic device processing circuitry 220. The skilled reader understands that in such an embodiment it is the computer program which is responsible for generating the nerve stimulation instructions, for causing the short range wireless communication protocol to send the nerve stimulation instructions to the nerve stimulation device, and for controlling the user electronic device processing circuitry to store data in the user specific data structure, to communicate with the internet and to display and process the set of acceleration measurements and the set of electrical pulse intensity measurements.

It is envisaged that the computer program is installable on the user electronic device via download from the Internet as an "app". Alternatively, it may be installable from a hardware device, such as a CD or solid state drive. Advantageously, the app is updatable via communication of the user electronic device 200 with the data network 300. This allows improvements and optimisations to the app, and hence the operation of the user electronic device 200 and the nerve stimulation device 100, to be easily performed.

The following are possible embodiments of the invention which may or may not be claimed:

1. A system for nerve stimulation comprising:
   a nerve stimulation device configured to execute a set of nerve stimulation instructions for generating electrical pulses for nerve stimulation of a patient; and
   a user electronic device, configured to:
      generate the set of nerve stimulation instructions; and
      send the set of nerve stimulation instructions wirelessly to the nerve stimulation device.
2. The system of embodiment 1, wherein the nerve stimulation device generates one or more electrical pulses for application to a patient corresponding to the set of nerve stimulation instructions.
3. The system of embodiment 2, wherein the set of nerve stimulation instructions comprises one or more instructions indicative of:
   a number of electrical pulses to be generated by the nerve stimulation device;
   an intensity of the one or more electrical pulses to be generated by the nerve stimulation device;
   a duration of each of the one or more of the electrical pulses to be generated by the nerve stimulation device; and
   an interval between the one or more electrical pulses to be generated by the nerve stimulation device.
4. The system of embodiment 3, wherein the intensity of the one or more electrical pulses is defined by an integer value in volts and/or amperes.
5. The system of any preceding embodiment, wherein the nerve stimulation device comprises an electrical pulse generator configured to generate the one or more electrical pulses.
6. The system of any preceding embodiment, wherein the user electronic device comprises a memory storing data of one or more preconfigured sets of nerve stimulation instructions.
7. The system of embodiment 6, wherein the user electronic device is configured to cause at least one set of the one or more preconfigured sets of nerve stimulation instructions to be selectable by a user from the one or more preconfigured sets of nerve stimulation instructions for sending as the nerve stimulation instructions to the nerve stimulation device.
8. The system of embodiment 6 or embodiment 7, wherein the one or more preconfigured sets of nerve stimulation instructions comprise one or more of:
   instructions for generating a Train of Four set of electrical pulses at the nerve stimulation device;
   instructions for generating a Post Tetanic Count set of electrical pulses at the nerve stimulation device; and
   instructions for generating a Twitch electrical pulse at the nerve stimulation device.
9. The system of any preceding embodiment, wherein the user electronic device is configured to be configurable with one or more user defined sets of nerve stimulation instructions.
10. The system of embodiment 9, wherein the user electronic device is configured to cause at least one set of the one or more user defined sets of nerve stimulation instructions to be selectable from the one or more user defined sets of nerve stimulation instructions for sending as the set of nerve stimulation instructions to the nerve stimulation device.
11. The system of any one of embodiments 2 to 10, wherein the nerve stimulation device comprises:
    a housing;
    at least two electrical conductors extending from the housing each adapted to be connected to an electrode and for supplying the one or more electrical pulses therebetween via a patient to which the electrodes are attached in use.
12. The system of embodiment 11, wherein the nerve stimulation device further comprises a connector extending from the housing connected to an acceleration sensor, wherein the acceleration sensor is adapted for attachment to the patient.
13. The system of embodiment 12, wherein the acceleration sensor is adapted for attachment to the patient's finger or eye.
14. The system of embodiment 12 or embodiment 13, wherein the acceleration sensor is configured to detect acceleration of one or more parts of the patient's body resulting from the one or more electrical pulses supplied to the patient.

15. The system of any one of embodiments 12 to 14, wherein the acceleration sensor is a tri-axial accelerometer.
16. The system of any one of embodiments 12 to 15, wherein the nerve stimulation device is configured to generate a set of one or more acceleration measurements from one or more accelerations detected by the acceleration sensor.
17. The system of embodiment 16, wherein the nerve stimulation device is configured to send the set of acceleration measurements to the user electronic device.
18. The system of embodiment 17, wherein the user electronic device is configured to display measured results corresponding to the acceleration measurements.
19. The system of embodiment 17 or embodiment 18, wherein the user electronic device is configured to store data of the measured results in a user specific data structure.
20. The system of embodiment 19, wherein the user electronic device is configured to load stored data of the measured results from the user specific data structure.
21. The system of embodiment 19 or embodiment 20, wherein the user electronic device is configured to:
   store the measured results in the user specific data structure in response to a user input at the user electronic device, and/or
   load the stored results from the user specific data structure in response to a user input at the user electronic device.
22. The system of any preceding embodiment, wherein the user electronic device is configured to store user inputted event data pertaining to a patient condition in a user specific data structure.
23. The system of any preceding embodiment, wherein the user electronic device is configured to communicate with the internet.
24. The system of any preceding embodiment, wherein the nerve stimulation device and user electronic device communicate with each other via a short range wireless communication protocol, e.g. Bluetooth, infrared, near field communication, ultraband and Zigbee.
25. The system of embodiment 24, wherein the nerve stimulation device and the user electronic device each comprise a short range wireless communication protocol transceiver for communicating via the short range wireless communication protocol, wherein the transceiver of the user electronic device is configured to send the set of nerve stimulation instructions to the transceiver of the nerve stimulation device.
26. The system of embodiment 24 or embodiment 25, wherein the nerve stimulation device is configured to be connected with a single user electronic device and communicate via the short range wireless communication protocol with only one user electronic device at any given time.
27. The system of embodiment 26, wherein the nerve stimulation device comprises a short range wireless protocol actuation device, wherein the nerve stimulation device is configured such that when the actuation device is actuated, the nerve stimulation device is placed into a pairing mode for a predetermined pairing time interval for pairing with the user electronic device.
28. The system of any preceding embodiment, wherein the user electrical device is configured to send to the nerve stimulation device one or more calibration instructions for generating electrical pulses in a calibration routine of a patient.
29. The system of embodiment 28, wherein the calibration instructions are predefined calibration instructions, the user electronic device comprises a memory storing the predefined calibration instructions, and wherein the user electronic device is configured to send the predefined calibration instructions to the nerve stimulation device.
30. The system of embodiment 28 when dependent on embodiment 17, wherein the user electronic device is configured to generate the calibration instructions based on the one or more acceleration measurements.
31. The system of any preceding embodiment, wherein the nerve stimulation device is configured to store built-in calibration instructions not sent from the user electronic device.
32. The system of embodiment 31, wherein the user electronic device is configured to send to the nerve stimulation device an instruction executable to cause the nerve stimulation device to execute the built-in calibration instructions.
33. The system of any one of embodiment 28 to embodiment 32, wherein the calibration instructions and/or built-in calibration instructions trigger the nerve stimulation device to generate a series of electrical pulses of increasing intensity and to record resulting acceleration measurements following generation of each electrical pulse or series of electrical pulses.
34. The system of embodiment 33, wherein the nerve stimulation device is configured to determine a maximum electrical pulse intensity as the intensity of an electrical pulse at which the resulting acceleration measurements reach a constant value.
35. The system of embodiment 33, wherein the user electronic device is configured to determine a maximum electrical pulse intensity as the intensity of an electrical pulse at which the resulting acceleration measurements reach a constant value.
36. The system of embodiment 34 or embodiment 35, wherein the user electronic device is configured to store the maximum electrical pulse intensity on a per user basis.
37. The system of any preceding embodiment, wherein the user electronic device is selected from one of: a mobile phone, a smartphone, tablet device or personal computer.
38. A nerve stimulation device, the nerve stimulation device comprising:
   a housing;
   a short range wireless communication transceiver configured to receive nerve stimulation instructions from a user electronic device,
   an electrical pulse generator configured to generate one or more electrical pulses corresponding to the received nerve stimulation instructions.
39. The nerve stimulation device of embodiment 38 further comprising:
   at least two electrical conductors extending from the housing each adapted to be connected to an electrode and for supplying the one or more electrical pulses therebetween via a patient to which the electrodes are attached in use.
40. The nerve stimulation device of embodiment 38 further comprising:
   at least two electrodes for supplying the one or more electrical pulses therebetween via a patient to which the electrodes are attached in use.
41. The nerve stimulation device of any one of embodiments 38 to 40, wherein the set of nerve stimulation instructions comprises one or more instructions indicative of:
   a number of electrical pulses to be generated by the nerve stimulation device;
   an intensity of the one or more electrical pulses to be generated by the nerve stimulation device;

a duration of each of the one or more of the electrical pulses to be generated by the nerve stimulation device; and an interval between the one or more electrical pulses to be generated by the nerve stimulation device.

42. The nerve stimulation device of embodiment 41, wherein the intensity of the one or more electrical pulses is defined by an integer value in volts and/or amperes.

43. The nerve stimulation device of any one of embodiments 38 to 42, wherein the nerve stimulation device further comprises a connector extending from the housing connected to an acceleration sensor, wherein the acceleration sensor is adapted for attachment to the patient.

44. The nerve stimulation device of embodiment 43, wherein the acceleration sensor is adapted for attachment to the patient's finger or eye.

45. The nerve stimulation device of embodiment 43 or embodiment 44, wherein the acceleration sensor is configured to detect acceleration of one or more parts of the patient's body resulting from the one or more electrical pulses supplied to the patient.

46. The nerve stimulation device of any one of embodiments 43 to 45, wherein the acceleration sensor is a tri-axial accelerometer.

47. The nerve stimulation device of any one of embodiments 43 to 46, wherein the nerve stimulation device is configured to generate a set of one or more acceleration measurements from one or more accelerations detected by the acceleration sensor.

48. The nerve stimulation device of embodiment 47, wherein the nerve stimulation device is configured to send the set of acceleration measurements to the user electronic device.

49. The nerve stimulation device of any one of embodiments 38 to 48, wherein the nerve stimulation device is configured to communicate via a short range wireless communication protocol, e.g. Bluetooth, infrared, near field communication, ultraband and Zigbee, with the user electronic device.

50. The nerve stimulation device of embodiment 49, wherein the nerve stimulation device comprises a short range wireless communication protocol transceiver for communicating via the short range wireless communication protocol, wherein the transceiver of the nerve stimulation device is configured to receive the set of nerve stimulation instructions from a transceiver of the user electronic device.

51. The nerve stimulation device of embodiment 49 or embodiment 50, wherein the nerve stimulation device is configured to be connected with a single user electronic device and communicate via the short range wireless communication protocol with only one user electronic device at any given time.

52. The nerve stimulation device of embodiment 51, wherein the nerve stimulation device comprises a short range wireless protocol actuation device, wherein the nerve stimulation device is configured such that when the actuation device is actuated, the nerve stimulation device is placed into a pairing mode for a predetermined pairing time interval for pairing with the user electronic device.

53. The nerve stimulation device of any one of embodiments 38 to 52, wherein the nerve stimulation device is configured to receive one or more calibration instructions for generating electrical pulses in a calibration routine of a patient from the user electronic device.

54. The nerve stimulation device of embodiment 53, wherein the calibration instructions are predefined calibration instructions, and wherein the nerve stimulation device is configured to receive the predefined calibration instructions from the user electronic device.

55. The nerve stimulation device of any one of embodiments 38 to 54, wherein the nerve stimulation device is configured to store built-in calibration instructions not sent from the user electronic device.

56. The nerve stimulation device of embodiment 55, wherein the nerve stimulation device is configured to receive from the user electronic device an instruction executable to cause the nerve stimulation device to execute the built-in calibration instructions.

57. The nerve stimulation device of any one of embodiment 38 to embodiment 56, wherein the calibration instructions and/or built-in calibration instructions trigger the nerve stimulation device to generate a series of electrical pulses of increasing intensity and to record resulting acceleration measurements following generation of each electrical pulse or series of electrical pulses.

58. The nerve stimulation device of embodiment 57, wherein the nerve stimulation device is configured to determine a maximum electrical pulse intensity as the intensity of an electrical pulse at which the resulting acceleration measurements reach a constant value.

59. A user electronic device, the user electronic device comprising:

processing circuitry configured to generate nerve stimulation instructions;

a short range wireless communication transceiver configured to send the nerve stimulation instructions to a nerve stimulation device based on a wireless communications protocol.

60. The user electronic device of embodiment 59, wherein the nerve stimulation device is configured to generate one or more electrical pulses for application to a patient corresponding to the set of nerve stimulation instructions.

61. The user electronic device of embodiment 60, wherein the set of nerve stimulation instructions comprises one or more instructions indicative of:

a number of electrical pulses to be generated by the nerve stimulation device;

an intensity of the one or more electrical pulses to be generated by the nerve stimulation device;

a duration of each of the one or more of the electrical pulses to be generated by the nerve stimulation device; and an interval between the one or more electrical pulses to be generated by the nerve stimulation device.

62. The user electronic device of embodiment 61, wherein the intensity of the one or more electrical pulses is defined by an integer value in volts and/or amperes.

63. The user electronic device of any one of embodiments 59 to 62 wherein the user electronic device comprises a memory storing data of one or more preconfigured sets of nerve stimulation instructions.

64. The user electronic device of embodiment 63, wherein the user electronic device is configured to cause at least one set of the one or more preconfigured sets of nerve stimulation instructions to be selectable by a user from the one or more preconfigured sets of nerve stimulation instructions for sending as the nerve stimulation instructions to the nerve stimulation device.

65. The user electronic device of embodiment 63 or embodiment 64, wherein the one or more preconfigured sets of nerve stimulation instructions comprise one or more of:

instructions for generating a Train of Four set of electrical pulses at the nerve stimulation device;

instructions for generating a Post Tetanic Count set of electrical pulses at the nerve stimulation device; and
instructions for generating a Twitch electrical pulse at the nerve stimulation device.

66. The user electronic device of any one of embodiments 59 to 65, wherein the user electronic device is configured to be configurable with one or more user defined sets of nerve stimulation instructions.

67. The user electronic device of embodiment 66, wherein the user electronic device is configured to cause at least one set of the one or more user defined sets of nerve stimulation instructions to be selectable from the one or more user defined sets of nerve stimulation instructions for sending as the set of nerve stimulation instructions to the nerve stimulation device.

68. The user electronic device of any one of embodiments 59 to 67, wherein the user electronic device is configured to receive from the nerve stimulation device a set of acceleration measurements generated by the nerve stimulation device from one or more accelerations detected by an acceleration sensor connected to the nerve stimulation device.

69. The user electronic device of embodiment 68, wherein the user electronic device is configured to display measured results corresponding to the acceleration measurements.

70. The user electronic device of embodiment 68 or embodiment 69, wherein the user electronic device is configured to store data of the measured results in a user specific data structure.

71. The user electronic device of embodiment 70, wherein the user electronic device is configured to load stored data of the measured results from the user specific data structure.

72. The user electronic device of embodiment 70 or embodiment 71, wherein the user electronic device is configured to:
    store the measured results in the user specific data structure in response to a user input at the user electronic device, and/or
load the stored results from the user specific data structure in response to a user input at the user electronic device.

73. The user electronic device of any one of embodiments 59 to 72, wherein the user electronic device is configured to store user inputted event data pertaining to a patient condition in a user specific data structure.

74. The user electronic device of any one of embodiments 59 to 73, wherein the user electronic device is configured to communicate with the internet.

75. The user electronic device of any one of embodiments 59 to 74, wherein the user electronic device is configured to communicate with the nerve stimulation device via a short range wireless communication protocol, e.g. Bluetooth, infrared, near field communication, ultraband and Zigbee.

76. The user electronic device of embodiment 24, wherein the user electronic device comprises a short range wireless communication protocol transceiver for communicating via the short range wireless communication protocol, wherein the transceiver of the user electronic device is configured to send the set of nerve stimulation instructions to a transceiver of the nerve stimulation device.

77. The user electronic device of any one of embodiments 59 to 76, wherein the user electrical device is configured to send to the nerve stimulation device one or more calibration instructions for generating electrical pulses in a calibration routine of a patient.

78. The user electronic device of embodiment 77, wherein the calibration instructions are predefined calibration instructions, the user electronic device comprises a memory storing the predefined calibration instructions, and wherein the user electronic device is configured to send the predefined calibration instructions to the nerve stimulation device.

79. The user electronic device of embodiment 77 when dependent on embodiment 68, wherein the user electronic device is configured to generate the calibration instructions based on the set of acceleration measurements.

80. The user electronic device of any one of embodiments 59 to 79, wherein the user electronic device is configured to send to the nerve stimulation device an instruction executable to cause the nerve stimulation device to execute built-in calibration instructions stored by the nerve stimulation device.

81. The user electronic device of any one of embodiment 77 to embodiment 80, wherein the calibration instructions and/or built-in calibration instructions are configured to trigger the nerve stimulation device to generate a series of electrical pulses of increasing intensity, and record resulting acceleration measurements following generation of each electrical pulse or series of electrical pulses.

82. The user electronic device of embodiment 81, wherein the user electronic device is configured to determine a maximum electrical pulse intensity as the intensity of an electrical pulse at which the resulting acceleration measurements reach a constant value.

83. The user electronic device of embodiment 82, wherein the user electronic device is configured to store the maximum electrical pulse intensity on a per user basis.

84. The user electronic device of any one of embodiments 59 to 83, wherein the user electronic device is selected from one of: a mobile phone, a smartphone, tablet device or personal computer.

85. A system comprising:
    the nerve stimulation device of any one of embodiments 38 to 58; and the user electronic device of any one of embodiments 59 to 84.

86. A method for controlling a nerve stimulation device comprising:
    generating a set of nerve stimulation instructions at a user electronic device;
        sending the set of nerve stimulation instructions wirelessly from the user electronic device to a nerve stimulation device for causing the nerve stimulation device to generate electrical pulses for nerve stimulation of a patient.

87. The method of embodiment 86, further comprising generating one or more electrical pulses for application to a patient corresponding to the set of nerve stimulation instructions at the nerve stimulation device.

88. The method of embodiment 87, wherein generating the set of nerve stimulation instructions comprises generating one or more instructions indicative of:
    a number of electrical pulses to be generated by the nerve stimulation device;
    an intensity of the one or more electrical pulses to be generated by the nerve stimulation device;
    a duration of each of the one or more of the electrical pulses to be generated by the nerve stimulation device; and
    an interval between the one or more electrical pulses to be generated by the nerve stimulation device.

89. The method of embodiment 88, wherein the intensity of the one or more electrical pulses is defined by an integer value in volts and/or amperes.

90. The method of any one of embodiments 86 to 89, further comprising generating one or more electrical pulses at an electrical pulse generator comprised by the nerve stimulation device.

91. The method of any one of embodiments 86 to 89, further comprising storing data of one or more preconfigured sets of nerve stimulation instructions in a memory comprised by the user electronic device.

92. The method of embodiment 91, further comprising:
causing at least one set of the one or more preconfigured sets of nerve stimulation instructions to be selectable by a user from the one or more preconfigured sets of nerve stimulation instructions for sending as the nerve stimulation instructions to the nerve stimulation device;
selecting at least one set of the one or more preconfigured sets of nerve stimulation instructions from the one or more preconfigured sets of nerve stimulation instructions for sending as the nerve stimulation instructions to the nerve stimulation device; and
sending the selected at least one set of the one or more preconfigured sets of nerve stimulation instructions as the nerve stimulation instructions to the nerve stimulation device.

93. The method of embodiment 91 or embodiment 92, wherein the one or more preconfigured sets of nerve stimulation instructions comprise one or more of:
instructions for generating a Train of Four set of electrical pulses at the nerve stimulation device;
instructions for generating a Post Tetanic Count set of electrical pulses at the nerve stimulation device; and
instructions for generating a Twitch electrical pulse at the nerve stimulation device.

94. The method of any one of embodiments 86 to 93, further comprising configuring the user electronic device with one or more user defined sets of nerve stimulation instructions.

95. The method of embodiment 94, further comprising:
causing at least one set of the one or more user defined sets of nerve stimulation instructions to be selectable from the one or more user defined sets of nerve stimulation instructions for sending as the set of nerve stimulation instructions to the nerve stimulation device;
selecting at least one set of the one or more user defined sets of nerve stimulation instructions from the one or more user defined sets of nerve stimulation instructions for sending as the set of nerve stimulation instructions to the nerve stimulation device; and
sending the selected at least one set of the one or more user defined sets of nerve stimulation instructions as the set of nerve stimulation instructions to the nerve stimulation device.

96. The method of any one of embodiments 87 to 95, further comprising supplying the one or more electrical pulses between at least two electrical conductors, each adapted to be connected to an electrode and extending from a housing of the nerve stimulation device, via a patient to which the electrodes are attached in use.

97. The method of embodiment 96, further comprising connecting an acceleration sensor to a connector extending from the housing of the nerve stimulation device, wherein the acceleration sensor is adapted for attachment to the patient.

98. The method of embodiment 97, wherein the acceleration sensor is adapted for attachment to the patient's finger or eye.

99. The method of embodiment 96 or embodiment 97, further comprising using the acceleration sensor to detect one or more accelerations of one or more parts of the patient's body resulting from the one or more electrical pulses supplied to the patient.

100. The method of any one of embodiments 97 to 99, wherein the acceleration sensor is a tri-axial accelerometer.

101. The method of any one of embodiments 97 to 100, further comprising generating a set of one or more acceleration measurements from one or more accelerations detected by the acceleration sensor.

102. The method of embodiment 101, further comprising sending the set of acceleration measurements from the nerve stimulation device to the user electronic device.

103. The method of embodiment 102, further comprising displaying measured results corresponding to the acceleration measurements at the user electronic device.

104. The method of embodiment 102 or embodiment 103, further comprising storing data of the measured results in a user specific data.

105. The method of embodiment 104, further comprising loading stored data of the measured results from the user specific data structure.

106. The method of embodiment 104 or embodiment 105, further comprising:
storing the measured results in the user specific data structure in response to a user input at the user electronic device, and/or
loading the stored results from the user specific data structure in response to a user input at the user electronic device.

107. The method of any one of embodiments 86 to 106, further comprising storing user inputted event data pertaining to a patient condition in a user specific data structure.

108. The method of any one of embodiments 86 to 106, further comprising the user electronic device communicating with the internet.

109. The method of any one of embodiments 86 to 106, further comprising the nerve stimulation device and user electronic device communicating with each other via a short range wireless communication protocol, e.g. Bluetooth, infrared, near field communication, ultraband and Zigbee.

110. The method of embodiment 109, wherein sending the nerve stimulation instructions to the nerve stimulation device comprises communicating the nerve stimulations instructions from a short range wireless communication transceiver of the user electronic device to a short range wireless communication transceiver of the nerve stimulation device via the short range wireless communication protocol.

111. The method of embodiment 109 or embodiment 110, further comprising connecting the nerve stimulation device with a single user electronic device, wherein the nerve stimulation device communicates via the short range wireless communication protocol with only one user electronic device at any given time.

112. The method of embodiment 111, further comprising placing the nerve stimulation device into a pairing mode for a predetermined pairing time interval for pairing with the user electronic device by actuating a short range wireless protocol actuation device comprised by the nerve stimulation device.

113. The method of any one of embodiments 86 to 112, further comprising sending one or more calibration instructions for generating electrical pulses in a calibration routine of a patient from the user electrical device to the nerve stimulation device.

114. The method of embodiment 113, wherein the calibration instructions are predefined calibration instructions, and the method further comprises sending the predefined calibration instructions stored in a memory of the user electronic device to the nerve stimulation device.

115. The method of embodiment 113 when dependent on embodiment 102, further comprising generating the calibration instructions at the user electronic based on the one or more acceleration measurements.

116. The method of any one of embodiments 86 to 115, further comprising storing built-in calibration instructions not sent from the user electronic device at the nerve stimulation device.

117. The method of embodiment 116, further comprising sending an instruction executable to cause the nerve stimulation device to execute the built-in calibration instructions nerve from the user electronic device to the nerve stimulation device.

118. The method of any one of embodiments 113 to 117, further comprising the calibration instructions and/or built-in calibration instructions triggering the nerve stimulation device to generate a series of electrical pulses of increasing intensity and to record resulting acceleration measurements following generation of each electrical pulse or series of electrical pulses.

119. The method of embodiment 118, further comprising the nerve stimulation device determining a maximum electrical pulse intensity as the intensity of an electrical pulse at which the resulting acceleration measurements reach a constant value.

120. The method of embodiment 118, further comprising the user electronic device determining a maximum electrical pulse intensity as the intensity of an electrical pulse at which the resulting acceleration measurements reach a constant value.

121. The method of embodiment 119 or embodiment 120, further comprising the user electronic device storing the maximum electrical pulse intensity on a per user basis.

122. The method of any one of embodiments 86 to 121, wherein the user electronic device is selected from one of: a mobile phone, a smartphone, tablet device or personal computer.

123. A computer program, comprising computer executable instructions which when executed by a processor of a user electronic device cause the user electronic device to perform the steps of any one of embodiments 86 to 122.

The components of the systems, devices and methods described herein may be utilised and/or manufactured in combination, or separately, in various ways which will be appreciate to the skilled person.

The invention claimed is:

1. A system for nerve stimulation comprising:
a nerve stimulation device configured to receive a nerve stimulation data packet comprising a set of nerve stimulation instructions for a complete series of one or more electrical pulses to deliver to a patient, the nerve stimulation device comprising
a housing,
an electrical pulse generator configured to generate the complete series of one or more electrical pulses,
at least two electrical conductors extending from the housing each adapted to be connected to an electrode attachable to a body part of the patient at a location separated from the housing, wherein the electrodes are adapted for applying the complete series of one or more electrical pulses to the body part of the patient, wherein the at least two electrical conductors are insulated conductive wires,
a connector extending from the housing connected to an acceleration sensor, wherein the acceleration sensor is adapted for attachment to the body part of the patient at the location separated from the housing and to detect movements of the body part as a result of the one or more electrical pulses, and
processing circuitry configured (1) to cause the electrical pulse generator to generate the complete series of one or more electrical pulses according to the nerve stimulation instructions in the nerve stimulation data packet, (2) to receive a signal from the acceleration sensor, the signal indicating the movements of the body part, and (3) to convert the signal into a set of one or more acceleration measurements;
a user electronic device configured to generate and send the nerve stimulation data packet wirelessly to the nerve stimulation device, and to receive from the nerve stimulation device an acceleration measurement data packet comprising the set of one or more acceleration measurements produced by the processing circuitry; and
a short range wireless communication transceiver in the nerve stimulation device configured to (1) receive the nerve stimulation data packet comprising the nerve stimulation instructions from the user electronic device, and (2) send the acceleration data packet comprising the set of one or more acceleration measurements produced by the processing circuitry to the user electronic device.

2. The system of claim 1, wherein the set of nerve stimulation instructions comprises one or more instructions indicative of:
a number of electrical pulses to be generated by the nerve stimulation device;
an intensity of the one or more electrical pulses to be generated by the nerve stimulation device;
a duration of each of the one or more of the electrical pulses to be generated by the nerve stimulation device; and
an interval between the one or more electrical pulses to be generated by the nerve stimulation device.

3. The system of claim 1, wherein the user electronic device comprises a memory storing data of one or more preconfigured sets of nerve stimulation instructions.

4. The system of claim 1, wherein the user electronic device is configured to send to the nerve stimulation device one or more calibration instructions for generating electrical pulses in a calibration routine of a patient.

5. The system of claim 4, wherein the calibration instructions are predefined calibration instructions, the user electronic device comprises a memory storing the predefined calibration instructions, and wherein the user electronic device is configured to send the predefined calibration instructions to the nerve stimulation device.

6. The system of claim 1, wherein the user electronic device is configured to send to the nerve stimulation device one or more calibration instructions for generating electrical pulses in a calibration routine of a patient, and wherein the user electronic device is configured to generate the calibration instructions based on the one or more acceleration measurements.

7. The system of claim 1, wherein the nerve stimulation device is configured to store built-in calibration instructions not sent from the user electronic device.

8. The system of claim 7, wherein the user electronic device is configured to send to the nerve stimulation device an instruction executable to cause the nerve stimulation device to execute the built-in calibration instructions.

9. The nerve stimulation system of claim 1, wherein the short range wireless communication transceiver is further configured to send a single acceleration measurements data packet to the user electronic device comprising a complete set of the one or more acceleration measurements resulting from applying the complete series of one or more electrical pulses to the body part of the patient.

10. A nerve stimulation device, the nerve stimulation device comprising:
   a housing;
   a short range wireless communication transceiver configured to receive a nerve stimulation data packet from a user electronic device, the nerve stimulation data packet comprising nerve stimulation instructions for a complete series of one or more electrical pulses;
   an electrical pulse generator configured to generate the complete series of one or more electrical pulses corresponding to the nerve stimulation instructions,
   at least two electrical conductors extending from the housing each adapted to be connected to an electrode attachable to a body part of the patient at a location separated from the housing, wherein the electrodes are adapted for delivering the complete series of one or more electrical pulses to the body part of the patient, wherein the at least two electrical conductors are insulated conductive wires,
   a connector extending from the housing and configured to be connected to an acceleration sensor, wherein the acceleration sensor is adapted for attachment to the body part of the patient at a location separated from the housing and to detect movements of the body part as a result of the complete series of one or more electrical pulses; and
   processing circuitry configured (1) to cause the electrical pulse generator to generate the complete series of one or more electrical pulses according to the nerve stimulation instructions, (2) to receive a signal from the acceleration sensor, the signal indicating the movements of the body part, (3) to convert the signal into a set of one or more acceleration measurements, and (4) to send an acceleration measurements data packet comprising the set of one or more acceleration measurements to the user electronic device via the short range wireless communication transceiver.

11. A system comprising:
   the nerve stimulation device of claim 10; and
   a user electronic device comprising
      a second processing circuitry configured to generate the nerve stimulation instructions, and
      a second short range wireless communication transceiver in the user electronic device configured to send the nerve stimulation instructions to the nerve stimulation device based on a wireless communications protocol.

12. A method for controlling the nerve stimulation device of claim 10 comprising:
   generating a set of nerve stimulation instructions at a user electronic device; and
   sending the set of nerve stimulation instructions wirelessly from the user electronic device to a nerve stimulation device for causing the nerve stimulation device to generate electrical pulses for nerve stimulation of a patient.

13. A computer program, comprising computer executable instructions which when executed by a processor of a user electronic device cause the user electronic device to perform the steps of claim 12.

14. The nerve stimulation device of claim 10, wherein the short range wireless communication transceiver is further configured to send a single acceleration measurements data packet to the user electronic device comprising a complete set of the one or more acceleration measurements resulting from applying the complete series of one or more electrical pulses to the body part of the patient.

* * * * *